United States Patent [19]

Fisher

[11] 4,237,279

[45] Dec. 2, 1980

[54] CRYSTALLINE 3-HYDROXYCEPHALOSPORIN SOLVATES

[75] Inventor: Jack W. Fisher, Indianapolis, Ind.

[73] Assignee: Eli Lilly and Company, Indianapolis, Ind.

[21] Appl. No.: 61,208

[22] Filed: Jul. 27, 1979

Related U.S. Application Data

[63] Continuation-in-part of Ser. No. 8,468, Feb. 1, 1979, abandoned.

[51] Int. Cl.³ .................................................. C07D 501/20
[52] U.S. Cl. ........................................ 544/16; 424/246
[58] Field of Search ........................... 544/16; 424/246

[56] References Cited

U.S. PATENT DOCUMENTS

| | | | |
|---|---|---|---|
| 3,947,414 | 3/1976 | Tensmeyer | 260/243 C |
| 3,947,415 | 3/1976 | Tensmeyer | 260/243 C |
| 3,957,773 | 5/1976 | Barton et al. | 260/243 C |
| 4,031,084 | 6/1977 | Kukolja et al. | 260/243 C |
| 4,044,002 | 8/1977 | Hatfield | 544/16 |
| 4,054,738 | 10/1977 | Yang | 544/26 |
| 4,060,688 | 11/1977 | Chauvette | 544/16 |
| 4,079,181 | 3/1978 | Tsuji et al. | 544/133 |
| 4,115,643 | 9/1978 | Kukolja et al. | 544/16 |

*Primary Examiner*—Nicholas S. Rizzo
*Attorney, Agent, or Firm*—Steven R. Lammert; Arthur R. Whale

[57] ABSTRACT

4'-Nitrobenzyl 7-phenoxyacetamide-3-hydroxy-3-cephem-4-carboxylate forms crystalline solvates with acetic acid, propionic acid and methylene chloride. The corresponding 3-hydroxy-3-cephem sulfoxide forms crystalline solvates with acetic acid, propionic acid and methanol. The described solvates allow for facile isolation and purification of 4'-nitrobenzyl 7-phenoxyacetamido-3-hydroxy-3-cephem-4-carboxylate and its 1-oxide.

7 Claims, No Drawings

CRYSTALLINE 3-HYDROXYCEPHALOSPORIN SOLVATES

Cross-Reference to Related Application

This application is a continuation-in-part of U.S. Patent application Ser. No. 8,468 filed Feb. 1, 1979, now abandoned.

Background and Summary of the Invention

3-Hydroxy-3-cephems and the corresponding sulfoxides have been described as intermediates in the chemical conversion of penicillins to cephalosporins substituted directly at C-3 with halo, alkoxy or other functional groups. Tsuji disclosed in U.S. Pat. No. 4,079,181 the preparation of 3-hydroxy-3-cephems from the penicillin sulfoxide derived bicyclic thiazolineazetidinones [U.S. Pat. No. 3,705,892]. 3-Hydroxy-3-cephems have also been prepared by ozonolysis of the corresponding 3-exomethylenecephams and penicillin sulfoxide derived 3-exomethylenecepham sulfoxides [U.S. Pat. No. 4,052,387] as described by Chauvette in U.S. Pat. Nos. 3,917,587 and 4,060,688. Also Hatfield recently described the reduction of 3-exomethylenecepham and 3-hydroxycephem sulfoxides to the corresponding sulfides using acetyl bromide as a reducing agent. The preparation of 3-halocephems and 3-hydroxycephem ethers from 3-hydroxycephems has been disclosed by Chauvette in U.S. Pat. Nos. 3,925,372 and 3,917,587 respectively. A clinically significant cephalosporin antibiotic which is prepared from 3-hydroxycephem intermediates is 7-[D-(2-amino-2-phenylacetamido)]-3-chloro-3-cephem-4-carboxylic acid.

This invention is directed to crystalline acetic acid, propionic acid, methylene chloride and methanol solvates of 4'-nitrobenzyl 7-phenoxyacetamido 3-hydroxy-3-cephem-4-carboxylate and the corresponding sulfoxide. The discovery of the present solvates allows for facile isolation and purification of 4'-nitrobenzyl 7-phenoxyacetamido-3-hydroxy-3-cephem-4-carboxylate and its 1-oxide.

Detailed Description of the Invention

The present invention is directed to 4'-nitrobenzyl 7-phenoxyacetamido-3-hydroxy-3-cephem-4-carboxylate solvates of the formula

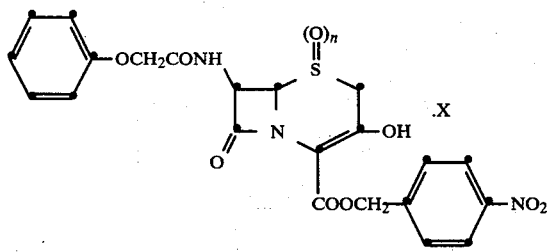

wherein n is 1 or 0; and X is $CH_3COOH$, $CH_3CH_2COOH$ or $CH_3OH$ when n is 1, and X is $CH_3COOH$, $CH_3CH_2COOH$ or $\frac{1}{2} CH_2Cl_2$ when n is 0.

The acetic acid solvates, a preferred embodiment of the present invention, contain 1 molar equivalent of acetic acid for each mole of 3-hydroxycephem. They are prepared simply by adding acetic acid to solutions containing 4'-nitrobenzyl 7-phenoxyacetamido-3-hydroxy-3-cephem-4-carboxylate or its 1-oxide. Depending, of course, on the concentration of the 3-hydroxycephem in solution and the particular solvent being used, the acetic acid solvate will crystallize spontaneously or it can be caused to crystallize by using conventional crystallization techniques such as lowering the solution temperature, adding an anti-solvent or seeding with crystals of the desired solvate or by using any combination of these crystallization techniques. The crystalline acetic acid solvates are isolated by filtration.

Solvents from which the acetic acid solvates of the present invention can be crystallized are generally those organic solvents in which the 3-hydroxycephem (sulfoxide) is soluble. Suitable solvents include halogenated hydrocarbons such as methylene chloride, chloroform, ethylene dichloride, and 1,1,2-trichloroethane; cyclic ethers such as tetrahydrofuran and dioxane; and amides such as dimethylformamide or dimethylacetamide. Alternatively the acetic acid solvates can be isolated from acetic acid itself. Anti-solvents for crystallizing the present acetic acid solvates from water immiscible solutions are lower aliphatic hydrocarbons such as pentane, hexane, cyclohexane or "petroleum ethers". Water can be employed advantageously in crystallizing the present acetic acid solvates from water miscible solvents such as dimethylformamide or acetic acid.

The solution from which the present acetic acid solvates are isolated can be reaction mixtures in which the 3-hydroxycephem (sulfoxide) has been prepared or such solutions can be prepared by simply dissolving the 3-hydroxy-3-cephem (sulfoxide), usually in an impure state, in the desired solvent for the purpose of purification by crystallization as the acetic acid solvate. The acetic acid solvate of 4'-nitrobenzyl 7-phenoxyacetamido-3-hydroxy-3-cephem-4-carboxylate 1-oxide which crystallized from acetic acid/water had a melting point of 138°–140° C.

The proponic acid solvates of the present invention are prepared, crystallized and isolated following procedures analogous to those described above for the acetic acid solvates with the exception, of course, of substituting propionic acid for acetic acid. The propionic acid solvate of 4'-nitrobenzyl 7-phenoxyacetamido-3-hydroxy-3-cephem-4-carboxylate which crystallized from a methylene chloride/propionic acid mixture had a melting point of 89°–91° C. while the corresponding 3-hydroxycephem sulfoxide propionic acid solvate (from dimethylformamide/water/propionic acid) melted at 149°–150° C.

The methylene chloride solvate of the present invention contains 0.5 molar equivalents of methylene chloride for each mole of 3-hydroxy-3-cephem ester. It is prepared typically by adding an anti-solvent such as hexane to methylene chloride solutions of 4'-nitrobenzyl 7-phenoxyacetamido-3-hydroxy-3-cephem-4-carboxylate to the cloud point with subsequent cooling and optional seeding of the solution.

Characteristic of each of the aforedescribed solvates is the fact that vacuum drying, even at elevated temperatures (30°–50° C.), fails to destroy the solvate. Heating the solvates to their fusion point will however free the bound solvent.

The methanol solvate of 4'-nitrobenzyl 7-phenoxyacetamido-3-hydroxy-3-cephem-4-carboxylate 1-oxide contains 1 molar equivalent of methanol for each mole of 3-hydroxycephem sulfoxide. It is prepared simply by slurrying a sample of the aforedescribed acetic acid solvate or propionic acid solvate of 4-nitrobenzyl 7- phenoxyacetamido-3-hydroxy-3-cephem-4-carboxylate 1-oxide in methanol for about 2–3 hours at room temperature. This methanol solvate is a "weaker" solvate than the corresponding acetic acid or propionic acid solvates. That is, vacuum drying of the methanol solvate at 30°–50° C. for about 12 to 24 hours provides an anhydrous, unsolvated sample of the 3-hydroxycephem sulfoxide. Thus, an impure sample of 4'-nitrobenzyl 7-phenoxyacetamido-3-hydroxy-3-cephem-4-carboxylate 1-oxide can be purified by first crystallizing it as its acetic acid or propionic acid solvate, preparing the methanol solvate by slurrying the acid solvate with methanol, and vacuum drying the methanol solvate to the anhydrous, unsolvated 3-hydroxycephem sulfoxide.

The preparation of 4'-nitrobenzyl 7-phenoxyacetamido-3-hydroxy-3-cephem-4-carboxylate and its 1-oxide are described in U.S. Pat. Nos. 4,044,002 and 4,060,688 respectively. U.S. Pat. Nos. 4,079,181, 3,917,587, 3,925,372 and 3,917,588 further describe the preparation of these compounds and their conversion to antibiotic compounds.

The following examples are provided to further illustrate the present invention.

EXAMPLE 1

4'-Nitrobenzyl 7-phenoxyacetamido-3-hydroxy-3-cephem-4-carboxylate methylene chloride solvate To a solution of 150 gm (298.7 mmol) of 4'-nitrobenzyl 7-phenoxyacetamido-3-hydroxy-3-cephem-4-carboxylate 1-oxide in 1500 ml of methylene chloride was added 75 ml (705 mmol) of amylene and then 54 ml (729 mmol) of acetyl bromide dropwise over a 10 minute period keeping the temperature at 20°–25° C. After 35 minutes at room temperature the reaction mixture was washed with water (2×1250 ml) and brine (1250 ml), dried over $Na_2SO_4$, and evaporated in vacuo to a volume of 400 ml. Hexane (800 ml) was added dropwise. The mixture was seeded when it turned cloudy during the hexane addition. The product crystallized. After 30 minutes the mixture was filtered. The crystalline solid was washed with 500 ml of 2:1/hexane:methylene chloride and dried at 40° under reduced pressure overnight to provide 135.1 gm of the title product: m.p. 75° C. (dec.)

nmr (DMSO d-6)δ3.56 (ABq, 2), 4.66 (s,2), 5.24 (d,1, J=4 Hz), 5.43 (s,2), 5.45 (q, 1, J=4 and 8 Hz), 5.77 (s, 1, ½ $CH_2Cl_2$), 7.0–8.4 (ArH) and 9.07 (d, 1, J=8 Hz).

Anal. Calcd. for $C_{22.5}H_{20}N_3O_8SCl$: C, 51.19; H, 3.82; Cl, 6.72; N, 7.96; O, 24.24; S, 6.07. Found: C, 51.15; H, 3.88; Cl, 6.46; N, 8.15; O, 24.20; S, 6.04.

EXAMPLE 2

4'-Nitrobenzyl 7-phenoxyacetamido-3-hydroxy-3-cephem-4-carboxylate acetic acid solvate (A) To a solution of 4'-nitrobenzyl 7-phenoxyacetamido-3-hydroxy-3-cephem-4-carboxylate 1-oxide, derived from ozonolysis of 15 gm of 4'-nitrobenzyl 7-phenoxyacetamido-3-methylenecepham-4-carboxylate sulfoxide, in 135 ml of methylene chloride at 15° C. was added 8.8 ml of amylene and 6.1 ml of acetyl bromide. After 2 hours an additional 1.86 ml of amylene and 1.3 ml of acetyl bromide were added. After 1 hour and again after 2 hours 25 ml of propylenecarbonate was added to the reaction mixture to increase the solubility of the 3-hydroxy sulfoxide. The reaction mixture was warmed to 30°–35° before the heat source was removed. After 6 hours at room temperature the reaction mixture was washed with water (4×500 ml) and then evaporated in vacuo to a weight of 55 gm. The title product crystallized after 75 ml of acetic acid was added to the reaction mixture. The crystalline product was filtered, washed and dried—6.93 gm. m.p. 116°–118° C.

A nuclear magnetic resonance spectrum of the dried product was identical to that of the known unsolvated material except for the presence of 1 equivalent of acetic acid (by nmr integration).

(B) In another experiment the unsolvated 4'-nitrobenzyl 7-phenoxyacetamido-3-hydroxy-3-cephem-4-carboxylate was obtained as a foam from the reduction of 4.0 grams of the corresponding sulfoxide with $PCl_3$. The product was dissolved in 25 ml of acetic acid. The acetic acid solvate (1.44 gm) crystallized from the acetic acid solution.

(C) To a solution of the 3-hydroxy cephem sulfoxide (7.52 gm, 5 mmol) in 75 ml of methylene chloride was added 4.33 gm (16.5 mmol) of triphenyl phosphine and 2.34 ml (33 mmol) of acetyl chloride. The mixture was refluxed (41° C.) for about 4 hours. The mixture was washed with water (5×50 ml) and brine (25 ml), dried over $Na_2SO_4$ and then evaporated in vacuo to 22 gm of a syrup. Attempts to crystallize the product failed until solution was treated with 2 ml of acetic acid. The mixture was diluted with 30 ml of 3:1/hexane:methylene chloride and filtered to afford after drying, 6.30 gm of the titled acetic acid solvate; m.p. 111°–115° C.

EXAMPLE 3

4'-Nitrobenzyl 7-phenoxyacetamido-3-hydroxy-3-cephem-4-carboxylate 1-oxide acetic acid solvate Impure 4'-nitrobenzyl 7-phenoxyacetamido-3-hydroxy-3-cephem-4-carboxylate 1-oxide (400 gm) was dissolved in 1000 ml of dimethylformamide. After 30 miuntes the dark solution was treated with 4 gm of Darco and then filtered through Hyflo to remove insolubles. The filtrate was diluted with 1200 ml of acetic acid and seeded. After about 15 minutes the product began to crystallize. Water (1200 ml) was added dropwise. Thirty minutes after water addition was complete the title product was filtered and washed with 1:1/water:acetic acid (500 ml) and water (500 ml). The product was air dried over night at 40° C. Yield—373.6 gm.

nmr (DMSO d-6)δ1.97 (s, 3, $CH_3COOH$), 4.09 (bs, 2), 4.78 (bs, 2), 5.12 (d, 1, J=5 Hz), 5.53 (bs, 2), 6.0 (q, 1, J=5 and 10 Hz), and 6.9–8.4 (ArH).

Anal. Calcd. for $C_{24}H_{23}N_3O_{11}S$: C, 51.34; H, 4.13; N, 7.48; O, 5.71. Found: C, 50.83; H, 4.12; N, 7.17; O, 5.23.

EXAMPLE 4

4'-Nitrobenzyl 7-phenoxyacetamido-3-hydroxy-3-cephem-4-carboxylate 1-oxide methanol solvate (A) To 100 ml of methanol was added 10 gm of 4'-nitrobenzyl 7-phenoxyacetamido-3-hydroxy-3-cephem-4-carboxylate 1-oxide acetic acid solvate. After 3 hours at room temperature the solution was cooled in ice of 30 minutes and filtered. The crystalline product was washed with cold methanol and dried—7.85 gm. The product softened at 87°–88° C. and then solidified before melting again at 118°–120° C. A nmr spectrum showed the product to contain 1 equivalent of methanol.

(B) 4'-Nitrobenzyl 7-phenoxyacetamido-3-hydroxy-3-cephem-4-carboxylate 1-oxide acetic acid solvate (derived from ozonolysis of the corresponding 3-methylenecepham sulfoxide in methylene chloride using acetic acid/water to effect crystallization) was suspended in 150 ml of methanol with seeding and stirring at room temperature for one hour. The recrystallized solid appeared finer than the acetic acid solvate crystals. The slurry was cooled in ice for 30 minutes and filtered. After washing the methanol solvate with cold methanol the solvate was dried over night at 40°–45° in a vacuum and then at 50°–55° C. for 4 hours affording 13.77 gm of a white powder m.p. 105°–110° C. (clear at 120° C.). An nmr spectrum showed the product to be free of solvate (acetic acid or methanol).

EXAMPLE 5

4'-Nitrobenzyl 7-phenoxyacetamido-3-hydroxy-3-cephem-4-carboxylate propionic acid solvate A 5.28 g portion of the methylene chloride solvate from Example 1 was dissolved in 25 ml of methylene chloride at room temperature. The resulting solution was diluted with 25 ml of propionic acid. The volume of the mixture was then reduced by evaporation in vacuo. Crystals of the title product formed during the evaporation. After 20 minutes the product was isolated by filtration, washed with 15 ml of propionic acid and dried in vacuo at 35° C. A total of 5.09 g of the title product was isolated.

nmr (CDCl$_3$)δ 1.16 (t, 3, C$\underline{H}_3$CH$_2$COOH), 2.4 (q, 2, CH$_3$C$\underline{H}_2$COOH), 3.45 (bs, 2, C$_2$-H), 2.96 (s, 2, C$_6$H$_3$OC$\underline{H}_2$), 5.13 (d, 1, J=4 Hz, C$_6$-H), 5.45 (ABq, 2, ester CH$_2$), 5.75 (q, 1, J=4 Hz and 8 Hz, C$_7$-H), and 6.9–8.4 (m, 10, N$\underline{H}$+ArH).

Anal. Calcd. for C$_{25}$H$_{25}$N$_3$O$_{10}$S: C, 53.66; H, 4.50; N, 7.51; S, 5.73. Found: C, 53.37; H, 4.41; N, 7.27; S, 5.65.

EXAMPLE 6

4'-Nitrobenzyl 7-phenoxyacetamido-3-hydroxy-3-cephem-4-carboxylate 1-oxide propionic acid solvate A 20 g portion of impure 4'-nitrobenzyl 7-phenoxyacetamido-3-hydroxy-3-hydroxy-3-cephem-4-carboxylate 1-oxide was dissolved in 50 ml of dimethylformamide (DMF) with warming. The resulting solution was filtered through a glass frit using 10 ml of DMF. Propionic acid (120 ml) was added to the filtrate. Crystallization was initiated by scratching the sides of the flask containing the mixture. Then 60 ml of water was added dropwise as the crystallization progressed. After stirring the mixture for 60 minutes at room temperature the crystalline product was filtered and washed with 2:1 propionic acid water. Vacuum drying at 45°–50° C. overnight gave 14.76 g of beige colored crystals: m.p. 149°–150° C.

nmr (DMSOd-6)δ.96 (t, 3, C$\underline{H}_3$CH$_2$COOH), 2.2 (q, 2, CH$_3$C$\underline{H}_2$COOH), 4.0 (bs, 2, C$_2$-H), 4.65 (bs, 2, C$_6$H$_5$OC$\underline{H}_2$—), 5.0 (d, 1, J=4 Hz, C$_6$-H), 5.45 (bs, 2, ester CH$_2$), 5.86 (q, 1, J=4 and 10 Hz, C$_7$-H) and 6.7–8.2 (ArH).

Anal. Calc. for C$_{25}$H$_{25}$N$_3$O$_{11}$S: C, 52.17; H, 4.38; N, 7.30; O, 30.58; S, 5.57. Found: C, 52.26; H, 4.26; N, 7.18; O, 30.72; S, 5.55.

I claim:

1. A cephalosporin solvate of the formula

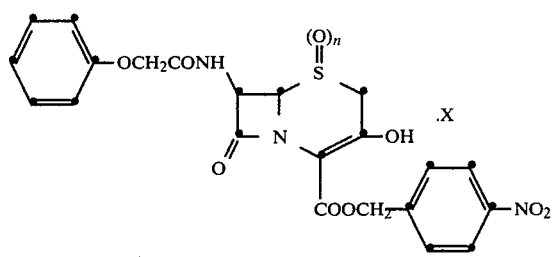

wherein n is 1 or 0; and X is CH$_3$COOH, CH$_3$CH$_2$COOH or CH$_3$OH when n is 1, and X is CH$_3$COOH, CH$_3$CH$_2$COOH or ½ CH$_2$Cl$_2$ when n is 0.

2. The cephalosporin acetic acid solvate of claim 1 of the formula

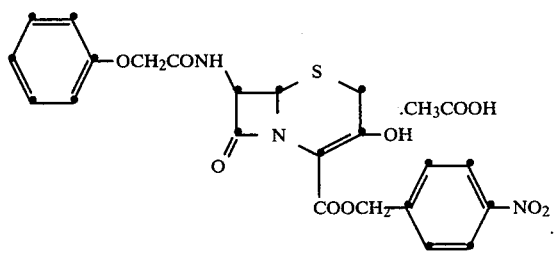

3. The cephalosporin sulfoxide acetic acid solvate of claim 1 of the formula

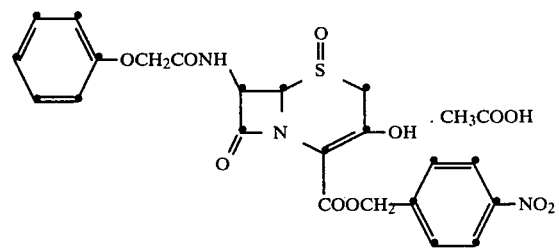

4. The cephalosporin methylene chloride solvate of claim 1 of the formula

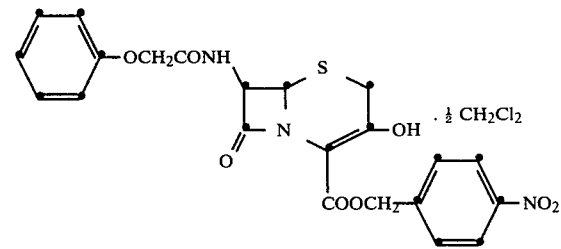

5. The cephalosporin methanol solvate of claim 1 of the formula

6. The cephalosporin propionic acid solvate of claim 1 of the formula
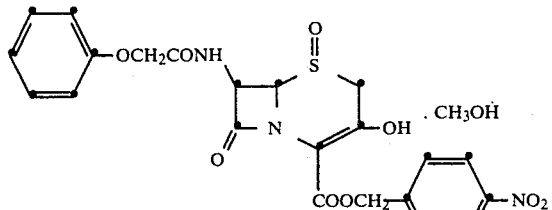
7. The cephalosporin sulfoxide propionic acid solvate of claim 1 of the formula
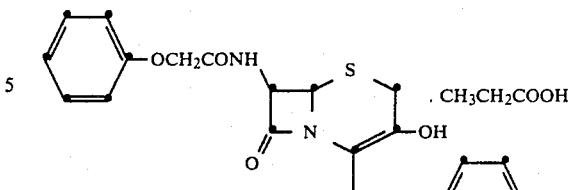
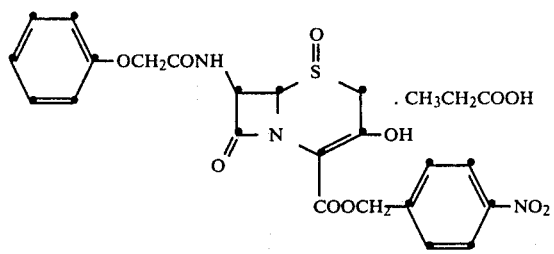
* * * * *